(12) United States Patent
Cheung

(10) Patent No.: US 8,523,987 B2
(45) Date of Patent: Sep. 3, 2013

(54) DUST ARRESTER AND METHOD FOR REMOVING DUST PARTICLES FROM AIR

(75) Inventor: Wong Tin Cheung, Kowloon (HK)

(73) Assignee: Yau Lee Innovative Technology Limited, Hong Kong (CN)

( * ) Notice: Subject to any disclaimer, the term of this patent is extended or adjusted under 35 U.S.C. 154(b) by 0 days.

(21) Appl. No.: 12/964,179

(22) Filed: Dec. 9, 2010

(65) Prior Publication Data

US 2011/0136214 A1 Jun. 9, 2011

Related U.S. Application Data

(60) Provisional application No. 61/267,970, filed on Dec. 9, 2009.

(51) Int. Cl.
  *B01D 47/14* (2006.01)
  *B01D 47/16* (2006.01)

(52) U.S. Cl.
  USPC ............... 96/272; 96/290; 96/281; 96/301; 96/302; 95/211; 95/218; 95/219; 55/356

(58) Field of Classification Search
  None
  See application file for complete search history.

(56) References Cited

U.S. PATENT DOCUMENTS

| | | | | |
|---|---|---|---|---|
| 3,733,061 A | * | 5/1973 | Bockman | 261/21 |
| 4,166,730 A | * | 9/1979 | Warhol | 96/267 |
| 4,312,646 A | * | 1/1982 | Fattinger et al. | 96/239 |
| 4,460,552 A | * | 7/1984 | Zakrzewski | 423/210 |
| 4,643,742 A | * | 2/1987 | Hammarskog | 95/16 |
| 5,908,493 A | * | 6/1999 | Krymsky | 96/333 |
| 5,935,300 A | * | 8/1999 | Niekerk | 95/212 |
| 6,533,844 B1 | * | 3/2003 | Hiltunen et al. | 95/271 |
| 2004/0231512 A1 | * | 11/2004 | Slayzak et al. | 95/211 |
| 2005/0081715 A1 | * | 4/2005 | Goodwin et al. | 95/211 |
| 2005/0284300 A1 | * | 12/2005 | Marusic | 96/271 |
| 2006/0185517 A1 | * | 8/2006 | Nagel | 96/275 |
| 2006/0249028 A1 | * | 11/2006 | Riccardi | 96/322 |
| 2007/0000386 A1 | * | 1/2007 | Decker | 95/211 |
| 2010/0251937 A1 | * | 10/2010 | Murray et al. | 106/705 |
| 2011/0048232 A1 | * | 3/2011 | Langford et al. | 95/149 |

FOREIGN PATENT DOCUMENTS

CN 2829860 10/2006

* cited by examiner

*Primary Examiner* — Duane Smith
*Assistant Examiner* — Pankti Patel
(74) *Attorney, Agent, or Firm* — Carlson, Gaskey & Olds, P.C.

(57) ABSTRACT

A dust arrester includes a housing with air inlet and air outlet, wherein the ambient air containing dust particles can be introduced into the housing via the air inlet and discharged from the housing via the air outlet. The dust arrester further includes a water trough placed in the bottom of the housing and a chaos effect generator including a nozzle and a material. The nozzle can spray water supplied from the water trough. The water sprayed interacts with the material to generate a chaos condition, so that the dust particles can be removed from the introduced air under the chaos condition.

7 Claims, 3 Drawing Sheets

DUST ARRESTER AND METHOD FOR REMOVING DUST PARTICLES FROM AIR

RELATED APPLICATION

This application claims priority to U.S. Provisional Application No. 61/267,970, which was filed Dec. 9, 2009.

TECHNICAL FIELD

The present disclosure relates to a dust arrester for air purification and a method for removing dust particles from air.

BACKGROUND

It is well known that air pollution is becoming an increasingly serious problem. A main source of air pollution is from construction and decoration projects in cities. Due to the inherent nature of construction and decoration engineering and urgent schedule that often requires various kinds of operations to be carried out within a limited space in a short time, the work sites of construction and decoration engineering are generally full of dust and undesirable odors. Therefore, not only the engineering staff at the working sites but also the neighboring residents will be exposed to and have to endure the poor environmental condition. Even after the projects are completed, building materials will still release harmful gases and odor, especially volatile organic compounds (VOC) such as formaldehyde, for a long time. These gases cannot be dispersed quickly in a natural way.

For example, construction projects create large amounts of dust, in particular respirable suspended particles (RSP). This RSP generally have a particle diameter less than 5 micrometers ($\mu m$). The RSP can be inhaled and reside in different positions in the respiratory tracts by means of collision, diffusion or sediment, which may lead to various respiratory diseases. Moreover, the RSP can remain in the air for a long time in a large area ranging from several to hundreds kilometers because of its extremely light weight.

Currently, dust filtering screens and/or dust collecting bags are widely used in ordinary industrial air purification systems, in which the dust particles are arrested on the dust filtering screens or in the dust collecting bags. Screens and bags provide simple solutions; however, the screens and bags must be maintained through periodic cleaning or replacement. The maintenance is very inconvenient and also uneconomical, especially in areas where large amount of dust is generated or present.

Another air purification method is known as wet-type air purification, in which the dust is removed by water spray. For example, CN2829860Y discloses a wet-type air purification method and dust removing device. In this device, the air flow passage is formed in a serpentine manner by a plurality of separating plates in order to enhance the dust removing efficiency.

SUMMARY OF THE INVENTION

This disclosure aims to provide a dust arrester that can avoid the above-mentioned defects existing in the prior art. Moreover, the examples herein further aim to provide a dust arrester and a method for removing dust particles from air in a high efficiency with simple structure at an affordable cost.

According to one embodiment, a dust arrester is provided, which includes: a housing with air inlet and air outlet, wherein the ambient air containing dust particles can be introduced into the housing via the air inlet and then discharged from the housing via the air outlet; a water trough arranged in the bottom of the housing; and a chaos effect generator including a nozzle and a material, wherein the nozzle can spray water supplied from the water trough, the water being interacted with the material to generate a chaos condition, so that the dust particles can be removed from the introduced air under the chaos condition.

According to an embodiment, the dust arrester creates an artificial chaos condition under the wind pressure generated by the extracted air. This kind of dust particle removing way is of high efficiency, and suitable for applications in construction and renovation sites or similar places. It can effectively trap the dust particles contained in the air, in particular the RSP, and thus purify the polluted air. The dust arrester is easy and economic to be operated, because no costly dust filtering screens or dust collecting bags are required and replacing/refilling water in the water trough is the only regular effort needed for continuous operation.

In an embodiment, the chaos condition is generated by the interaction of spraying water and a material made from plastics. Advantageously, the plastic material is made in a shape of spiral, preferably irregular spiral. This arrangement can ensure a sufficient interaction between water and plastic material, and thus can enhance the chaos condition generated and significantly increase the dust particle removing efficiency.

In another advantageous embodiment, the dust arrester is arranged such that the air is extracted into the chaos effect generator along a direction perpendicular to the longitudinal axis of the chaos effect generator. In such way, the effect of the chaos condition generated will be increased to some extent. Advantageously, the chaos effect generator can drive the extracted air into rotational movement, so that the chaos condition is generated under a rotation state. Alternatively, the chaos effect generator itself can be driven into rotational movement so that the chaos condition is generated under a rotation state. This arrangement can further enhance the effect of chaos condition generated and thus increase the dust particle removing efficiency.

In a particular embodiment, the housing consists of a hollow interior housing and a hollow exterior housing that are coaxial with each other. In this case, the air inlet is located in the peripheral of the exterior housing while the air outlet is formed by the open end of the interior housing. Of course, the positions of the interior and exterior housing can be exchanged with each other if needed.

In an example, the interior housing is shorter than the exterior housing, and the low end of the interior housing is supported by a supporting plate secured to the inner surface of the exterior housing. Advantageously, the chaos effect generator as a whole is placed on the supporting plate within the space formed between the exterior housing and the interior housing. This is especially advantageous for achieving a compact structure. Moreover, in this case, the chaos effect generator can be pre-fabricated in advance and then placed on the supporting plate. Therefore, the assembly procedure of the device is simplified.

In a further embodiment, an additional chaos effect generator is installed in the region of the supporting plate surrounded by the interior housing. Therefore, the air extracted into the dust arrester will pass through two stage chaos conditions, so that the dust particles can be removed almost entirely.

Optionally, the dust arrester further includes at least one of ozone generator, active carbon filter and enzyme odor remover, in order to remove some specifically undesirable smells in the extracted air.

According to another aspect, a method for removing dust particles from air is provided, including: introducing air into a housing; generating a chaos condition in the housing and removing dust particles from the introduced air under the chaos condition; and discharging the treated air from the housing.

In an embodiment of the method, the chaos condition is generated by the interaction of water and plastic material, which in particular is formed in a shape of irregular spiral.

In another embodiment, the chaos condition is generated under rotation state.

Other exemplary embodiments and advantages may be ascertained by reviewing the present disclosure and the accompanying drawing.

BRIEF DESCRIPTION OF THE DRAWINGS

The accompanying drawings are provided to facilitate the understanding of the disclosure. It constitutes a part of the specification but does not restrict the scope of the disclosure in any aspect. In the drawings.

DESCRIPTION OF THE INVENTION

Figure 1:
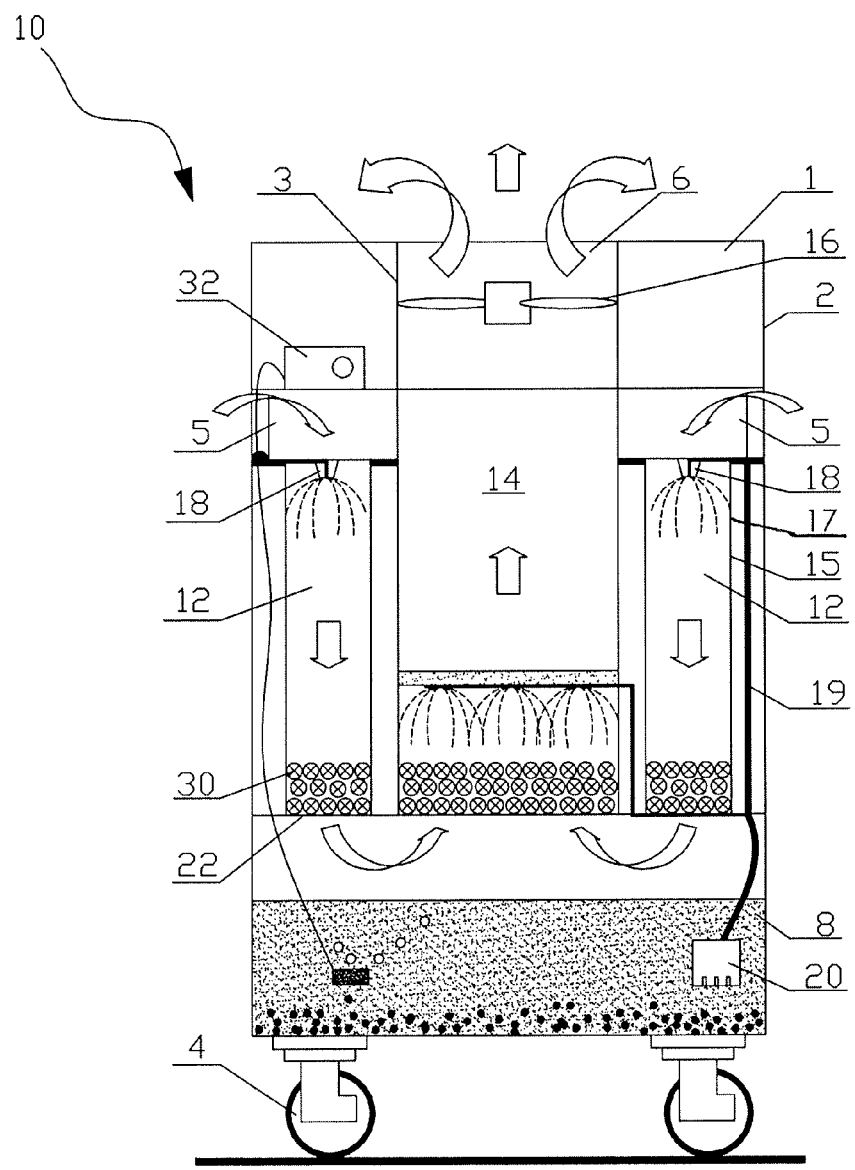
FIG. 1 shows the dust arrester in a cutaway view.

As shown in FIG. 1, an exemplary dust arrester 10 includes a housing 1. In an embodiment, the housing 1 is preferably a cylindrical body made from metal, which, in the embodiment as shown, consists of two hollow cylindrical bodies, i.e., an exterior housing 2 and an interior housing 3 that are arranged coaxially with each other. The interior housing 3 is shorter than the exterior housing 2, and is supported by a supporting plate 22 fixed to the inner surface of the exterior housing 2.

The supporting plate 22 is perforated so as to facilitate air flowing therethrough. A water trough 8 accommodating a certain volume of water is arranged at the bottom of the exterior housing 2. The water trough 8 is may be made in the form of a drawer for the convenience of cleaning and water refilling. Moreover, at the bottom surface of the exterior housing 2 there are a plurality of truckles 4, so that the whole device can be moved easily. For instance, there may be four truckles 4.

The exterior housing 2 is provided with air inlets at the upper part thereof. In the embodiment as shown in FIG. 1, the air inlets are two air inlets 5 arranged in two positions diametrically opposing each other, respectively. However, it is also conceivable to arrange more than two air inlets 5 along the peripheral direction of the exterior housing 2.

In the dust arrester 10, suction fans (not shown in the drawing) are provided adjacent to the air inlets 5 for moving the ambient surrounding air into the dust arrester 10 through the air inlets 5. The inflow air enters into the space 12 formed between the exterior housing 2 and the interior housing 3, and then flows into the overhead clearance of the water trough 8 after passing through the supporting plate 22. Afterwards, air enters into the central passage 14 defined by the interior housing 3 after passing through the supporting plate 22 again, and finally discharges from the dust arrester 10 through an air outlet 6 defined by the upper port of the interior housing 3.

This air flow motion is illustratively shown with the arrows in FIG. 1. To enhance the air flow motion inside the dust arrester 10, an exhaust fan 16 is arranged adjacent to the air outlet 6 in the central passage 14.

A chaos effect generator 15 is provided in the space 12 between the exterior housing 2 and interior housing 3. The chaos effect generator 15 may be made as a hollow discrete cylinder having a wall 17, which can be prefabricated in advance and then inserted in to the space 12 easily. In particular, the chaos effect generator 15 includes a nozzle 18 at the top portion thereof. The nozzle 18 is connected to a submersible pump 20 placed within the water trough 8 by means of pipe 19.

In operation, the submersible pump 20 supplies water from the water trough 8 to the nozzle 18, which in turn sprays water downwards at a certain rate. In an embodiment, the chaos effect generator 15 is a double-walled cylinder, so that the pipe 19 can run between the two walls of the chaos effect generator 15 between the nozzle 18 and the water trough 8. In such way, a very compact structure is obtained.

In addition, the chaos effect generator 15 further includes material 30 located on the supporting plate 22, which is approximately vertically aligned with the nozzle 18. Thus, water from the nozzle 18 is directly sprayed to the material 30. In one example, the material 30 is arranged such that the area between the exterior housing 2 and the interior housing 3 on the supporting plate 22 is entirely occupied by the material 30.

In operation of the dust arrester 10, water is sprayed from the nozzle 18 in the downward direction and then interacts with the material 30 on the supporting plate 22. As the result of the interaction of water and the material 30, a chaos condition is generated. The wind pressure originated from the air flow will also contribute to the generation of the chaos condition to some extent. After the ambient air containing dust particles is moved into the space 12, the chaos condition will enable the dust particles contained in the extracted air to be removed therefrom in an efficient way. The removed dust particles then fall into water in the water trough 8, as shown at the bottom. The purified air without dust particles flows upwards into the central passage 14, and then discharges out of the dust arrester 10 via the air outlet 6. Therefore, the interaction of water sprayed from the nozzle 18 and the material 30 leads to efficient removal of dust particles, in particular RSP, from the inflow air.

The chaos condition is generated from the interaction of fluid, e.g. water, sprayed from the nozzle 18 and the material 30. The material 30 can generate various physical forms of chaos condition when interacting with fluid molecule, e.g. water molecule, and is already known in the art. In one embodiment, the material 30 is plastic media having irregular shapes. For example, the plastic media can be a polyvinyl chloride (PVC) made, meta-level, randomly packed media that provides extraordinarily high surface area per unit volume, resulting in high transfer efficiency so as to permit large population of microorganisms to reside on its surface and form a biological film. The biological film grows on the surface with continuous water flow through the plastic media and substrates removal in the process. Advantageously, the material is of an irregular spiral shape. As an example, the material can be the product with name of "Fujino spirals" as disclosed in U.S. Pat. No. 5,609,344. Of course, other material that can generate similar chaos condition can be used also.

To achieve a desirable chaos condition, the water sprayed is in form of spray mist, and may be in the form of shower, so that the water droplets or molecules can be evenly distributed and then flow through the surface of the spiral shape plastic media. In one example, water is sprayed from the nozzle 18 at a rate of about 2 meters per second (m/s).

Figure 2:
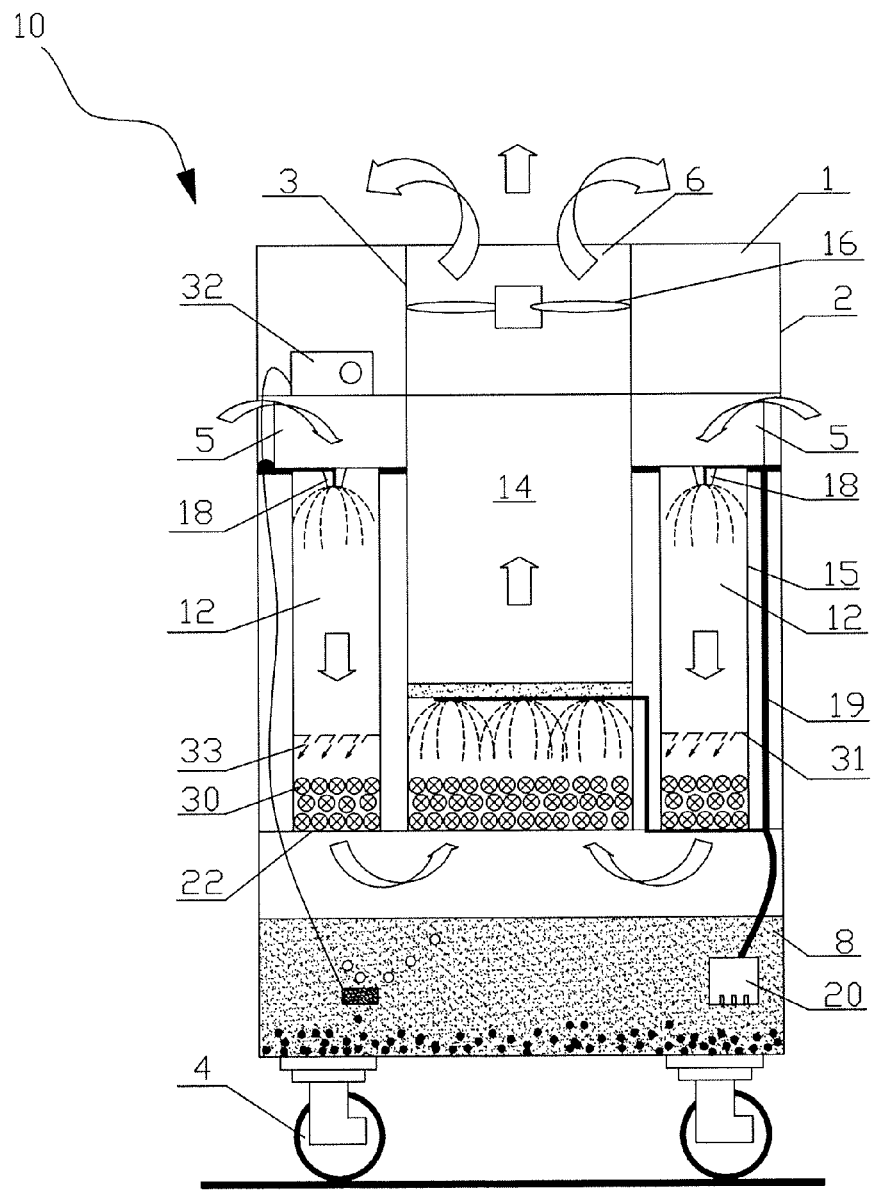
FIG. 2 shows another example dust arrester in a cutaway view.

In another embodiment shown in FIG. 2, the chaos effect generator 15 can drive the exhausted air in rotational movement. To this end, the chaos effect generator 15 further includes a panel 31 therein above the material 30. This panel 31 is provided with a plurality of turning vane type openings 33 in parallel with each other. For example, the openings 33 are of elongated slots and form an angle with the radius direction of the panel. In this case, air will be driven in rotational movement after passing through the panel 31.

Figure 3:
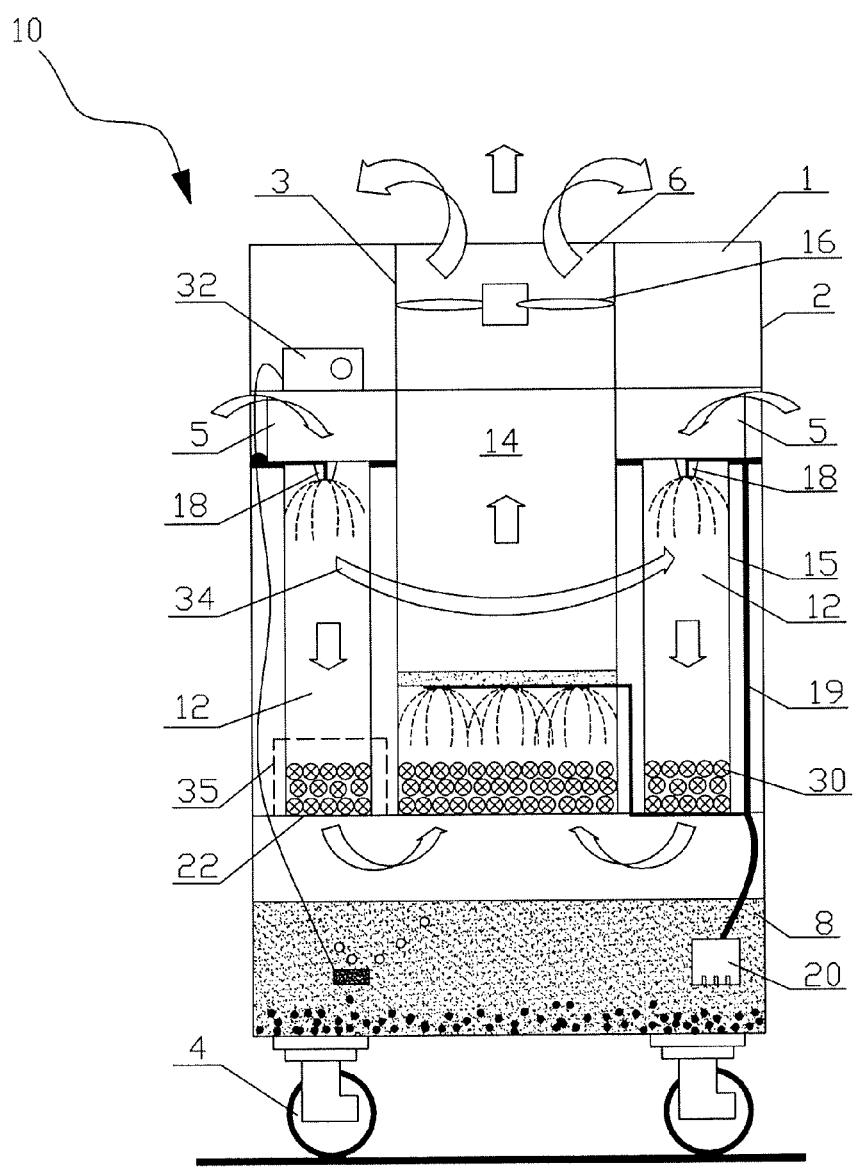
FIG. 3 shows another example dust arrester in a cutaway view.

Alternatively, the chaos effect generator 15 can be driven in rotational movement, as represented generally by the arrows 34 in FIG. 3. This can be achieved by providing a motor 35 to drive the supporting plate 22, and thus the chaos effect generator 15 placed thereon, into rotational movement. Therefore, the chaos condition generated under rotation state can further increase the dust particle removal efficiency.

In one embodiment of the dust arrester 10, the exterior housing 2 has a diameter of 550 millimeters (mm) and a height of 1200 mm, e.g. the ratio between the height and diameter of the housing is about 1200/550 or 2.2:1. The ambient air is extracted into the dust arrester 10 at a rate of 0.2 cubic meters per second (m3/s). The volume of the water trough 8 is 25 liters (L). The power of the dust arrester 10 is 380 watts (W). The entire device weighs 45 kilograms (kg). Tests show that at the construction sites with rich dust particles, the water consumption of the dust arrester 10 under the condition of continuous operation in a day is 18 L.

In the dust arrester 10, it is unnecessary to clean or replace a costly dust filtering screen or dust collecting bag. The dust arrester 10 can remove the dust particles in the introduced air in an efficient and low-cost manner as long as water in the water trough 8 is refilled in a regular period.

In addition, a built-in ozone generator 32 can be provided within the dust arrester 10, which can be activated to absorb volatile organic compounds (VOC) and other odors in the air. If necessary, an active carbon filter or an enzyme odor remover can be additionally provided in the dust arrester 10 to absorb or adsorb other particular odors.

In an example, an additional chaos effect generator 15 is arranged in the region of the supporting plate 22 within the central passage 14. As shown in FIG. 1, the additional chaos effect generator can similarly include one or more, three as shown, nozzles 18 and plastic media of irregular spiral shape on the supporting plate 22. In this manner, the air flowing into the dust arrester 10 will pass through two stages of chaos conditions, so that the dust particles contained in the air can be removed in a more sufficient manner.

It should be noted that the foregoing only describes the basic conception and arrangement of the dust arrester. One skilled in the art can make improvements based on the above-mentioned structure. For example, the positions of air inlet and air outlet can be exchanged with each other; in other words, in an alternative embodiment air is introduced into the device from the interior housing while discharged from the exterior housing. Moreover, although in the foregoing examples are described with water as the example of media for generating chaos, other type of fluid can be used also. Thus, the term "water" should be understood as all the liquids that can generate chaos when interacting with the selected material.

It shall be noted that the foregoing examples have been provided merely for the purpose of explanation and are in no way to be construed as limiting of the present invention in whether way. While the disclosure has been described with reference to an exemplary embodiment, it is understood that the words which have been used herein are the words of description and illustration, rather than that of limitation. Changes may be made, within the purview of the appended claims, as presently stated and as amended, without departing from the scope and spirit of the present invention in its aspects. Although the disclosure has been described herein with reference to particular means, materials and embodiments, the disclosure is not intended to be limited to the particulars herein; rather, the disclosure extends to all functionally equivalent structures, methods and uses, such as are within the scope of the appended claims.

What is claimed is:

1. A dust arrester, including:
   a housing having an exterior body, said exterior body having an air inlet, and an air outlet wherein ambient air containing particles is introduced into the housing via the air inlet and then discharged, after diminishing particle content therein, from the housing via said air outlet;
   a central passageway within said housing and in fluid communication transversely with said air inlet and coaxially with said air outlet;
   a water trough extending across a bottom of the housing below said central passageway and said housing, wherein said water trough is a drawer; and
   a plurality of first chaos effect generators, each first chaos effect generator discretely defined by a wall that is disposed between said exterior body and said central passageway, each said chaos effect generator including a nozzle and a material, wherein the nozzle is operable to spray water supplied from the water trough, the water interacting with the material to generate a chaos condition such that the particles are removed from the ambient air containing particles under a generated chaos condition.

2. The dust arrester of claim 1 wherein said housing is portable and includes a wheel mounted to said portable housing to move said housing.

3. The dust arrester of claim 1 further comprising:
   a second chaos effect generator, said second chaos effect generator disposed within said central passageway said second chaos effect generator including a nozzle and a material, wherein the nozzle is operable to spray water supplied from the water trough, the water interacting with the material to generate a chaos condition such that the particles are removed from the ambient air containing particles under a generated chaos condition.

4. The dust arrester including:
   a housing having an exterior body, said exterior body having an air inlet, and an air outlet wherein ambient air containing particles is introduced into the housing via the air inlet and then discharged, after diminishing particle content therein, from the housing via said air outlet;
   a central passageway within said housing and in fluid communication transversely with said air inlet and coaxially with said air outlet;
   a water trough extending across a bottom of the housing below said central passageway and said housing; and
   a plurality of first chaos effect generators, each first chaos effect generator discretely defined by a wall that is disposed between said exterior body and said central passageway, each said chaos effect generator including a nozzle and a material, wherein the nozzle is operable to spray water supplied from the water trough, the water interacting with the material to generate a chaos condition such that the particles are removed from the ambient air containing particles under a generated chaos condition a second chaos effect generator, said second chaos effect generator disposed within said central passageway said second chaos effect generator including a nozzle and a material, wherein the nozzle is operable to spray water supplied from the water trough, the water interacting with the material to generate a chaos condition such that the particles are removed from the ambient air containing particles under a generated chaos condition, wherein said second chaos generator has less distance between the nozzle and the material than a distance between the nozzle and the material of each first chaos generator.

5. The dust arrester of claim 3 wherein a bottom of said second chaos generator is in plane with a bottom of said first chaos generator.

6. The dust arrester of claim 1 wherein the plastic media is in a shape of irregular spiral.

7. The dust arrester including:

a housing having an exterior body, said exterior body having an air inlet, and an air outlet wherein ambient air containing particles is introduced into the housing via the air inlet and then discharged, after diminishing particle content therein, from the housing via said air outlet, wherein a ratio of a height of the housing to a diameter of the housing is about 2.2:1;

a central passageway within said housing and in fluid communication transversely with said air inlet and coaxially with said air outlet;

a water trough extending across a bottom of the housing below said central passageway and said housing; and a plurality of first chaos effect generators, each first chaos effect generator discretely defined by a wall that is disposed between said exterior body and said central passageway, each said chaos effect generator including a nozzle and a material, wherein the nozzle is operable to spray water supplied from the water trough, the water interacting with the material to generate a chaos condition such that the particles are removed from the ambient air containing particles under a generated chaos condition.

* * * * *